(12) United States Patent
Anklin et al.

(10) Patent No.: US 10,533,884 B2
(45) Date of Patent: Jan. 14, 2020

(54) MEASURING TRANSDUCER OF VIBRATION-TYPE

(71) Applicant: Endress + Hauser Flowtec AG, Reinach (CH)

(72) Inventors: Martin Josef Anklin, Dornach (CH); Gerhard Eckert, Grenzach-Wyhlen (DE); Christian Schutze, Basel (CH); Ennio Bitto, Aesch (CH); Christof Huber, Bern (CH); Claude Hollinger, Aesch (CH); Alfred Rieder, Landshut (DE); Michael Kirst, Lorrach (DE)

(73) Assignee: ENDRESS + HAUSER FLOWTEC AG, Reinach (CH)

( * ) Notice: Subject to any disclaimer, the term of this patent is extended or adjusted under 35 U.S.C. 154(b) by 0 days.

(21) Appl. No.: 15/535,515

(22) PCT Filed: Nov. 9, 2015

(86) PCT No.: PCT/EP2015/076023
§ 371 (c)(1),
(2) Date: Jun. 13, 2017

(87) PCT Pub. No.: WO2016/096243
PCT Pub. Date: Jun. 23, 2016

(65) Prior Publication Data
US 2017/0343404 A1 Nov. 30, 2017

(30) Foreign Application Priority Data
Dec. 18, 2014 (DE) .......... 10 2014 119 073

(51) Int. Cl.
*G01F 1/84* (2006.01)
*G01N 11/16* (2006.01)
*G01N 9/00* (2006.01)

(52) U.S. Cl.
CPC .......... *G01F 1/8468* (2013.01); *G01F 1/8404* (2013.01); *G01F 1/8409* (2013.01);
(Continued)

(58) Field of Classification Search
CPC .................. G01F 1/84; G01F 1/15
See application file for complete search history.

(56) References Cited

U.S. PATENT DOCUMENTS

| 4,962,671 A | 10/1990 | Stansfeld |
|---|---|---|
| 6,647,807 B2 | 11/2003 | Drahm |

(Continued)

FOREIGN PATENT DOCUMENTS

| CN | 101128721 A | 2/2008 |
|---|---|---|
| DE | 10220827 A1 | 11/2003 |

(Continued)

OTHER PUBLICATIONS

German Search Report, German Patent Office, Munich, DE, dated Jul. 31, 2015.

(Continued)

*Primary Examiner* — Jewel V Dowtin
(74) *Attorney, Agent, or Firm* — Bacon & Thomas, PLLC

(57) ABSTRACT

A measuring transducer for registering and/or monitoring at least one process variable of a flowable medium guided in a pipeline, which at least includes: a housing module, which is mechanically coupled with the pipeline via an inlet end and an outlet end, and a sensor module having at least one measuring tube held oscillatably at least partially in the housing module and caused, at least at times, to oscillate. The at least one component of the housing module and/or of the sensor module is manufactured by means of a generative method and method for manufacturing at least one component of a measuring transducer, which method includes manufacturing the at least one component by means of a primary forming process, especially by means of a layered applying and/or melting-on of a powder, especially a metal powder, based on a digital data set, which gives at least the shape and/or the material and/or the structure of the at least one component.

15 Claims, 7 Drawing Sheets

(52) U.S. Cl.
CPC ........... *G01N 9/002* (2013.01); *G01N 11/167* (2013.01); *G01N 2009/006* (2013.01); *G01N 2291/02818* (2013.01)

(56) References Cited

U.S. PATENT DOCUMENTS

| | | | |
|---|---|---|---|
| 7,171,860 B2 | 2/2007 | Gebhardt | |
| 7,634,939 B2* | 12/2009 | Drahm | G01F 1/8409 73/54.25 |
| 7,784,360 B2* | 8/2010 | Henry | G01F 1/74 73/861.356 |
| 7,971,494 B2 | 7/2011 | Hussain | |
| 8,590,400 B2 | 11/2013 | Keita | |
| 8,695,438 B2* | 4/2014 | Hays | G01F 1/8472 73/861.356 |
| 9,046,400 B2* | 6/2015 | Henry | G01F 1/8404 702/45 |
| 9,109,032 B2 | 8/2015 | Voigt | |
| 9,194,731 B2 | 11/2015 | Chatzikonstantinou | |
| 9,360,358 B2* | 6/2016 | Wang | G01F 1/8409 |
| 2006/0201260 A1 | 9/2006 | Drahm | |
| 2011/0088486 A1 | 4/2011 | Keita et al. | |
| 2012/0123705 A1 | 5/2012 | Drahm | |
| 2013/0116941 A1* | 5/2013 | Lie-Nielsen | G01F 15/063 702/46 |
| 2014/0260668 A1 | 9/2014 | Liu | |
| 2015/0306789 A1 | 10/2015 | Regen et al. | |
| 2017/0343404 A1 | 11/2017 | Anklin | |

FOREIGN PATENT DOCUMENTS

| | | |
|---|---|---|
| DE | 102007038507 A1 | 2/2009 |
| DE | 102008002217 A1 | 12/2009 |
| DE | 102008025869 A1 | 12/2009 |
| DE | 102010044179 A1 | 5/2012 |
| DE | 202012012729 U1 | 11/2013 |
| DE | 102012016490 A1 | 12/2013 |
| DE | 102012016490 A1 | 12/2015 |
| DE | 102014119073 A1 | 6/2016 |
| EP | 0317340 A2 | 5/1989 |
| EP | 0849568 A1 | 6/1998 |
| EP | 1130367 A1 | 9/2001 |
| EP | 1528373 A2 | 5/2005 |
| EP | 1985975 A2 | 10/2008 |
| WO | 2007057385 A1 | 5/2007 |
| WO | 2011031270 A1 | 3/2011 |

OTHER PUBLICATIONS

International Search Report, EPO, The Netherlands, dated Feb. 5, 2016.
English Translation of the International Preliminary Report on Patentability, WIPO, Geneva, CH, dated Jun. 29, 2017.
Chinese Office Action in corresponding Chinese Application No. 201580069658.0, dated Dec. 29, 2018.
Search Report dated Aug. 23, 2019 in corresponding European Application No. 15791602.4.
Eine SWOT-Analyse zum Einsatz der Additiven Fertigung für metallische Bauteile—BHM (2015) vol. 160(1): 15-20.
Office Action issued by European Office dated Aug. 23, 2019 in corresponding European Patent No. 15791602.4-1001/3234516.

* cited by examiner

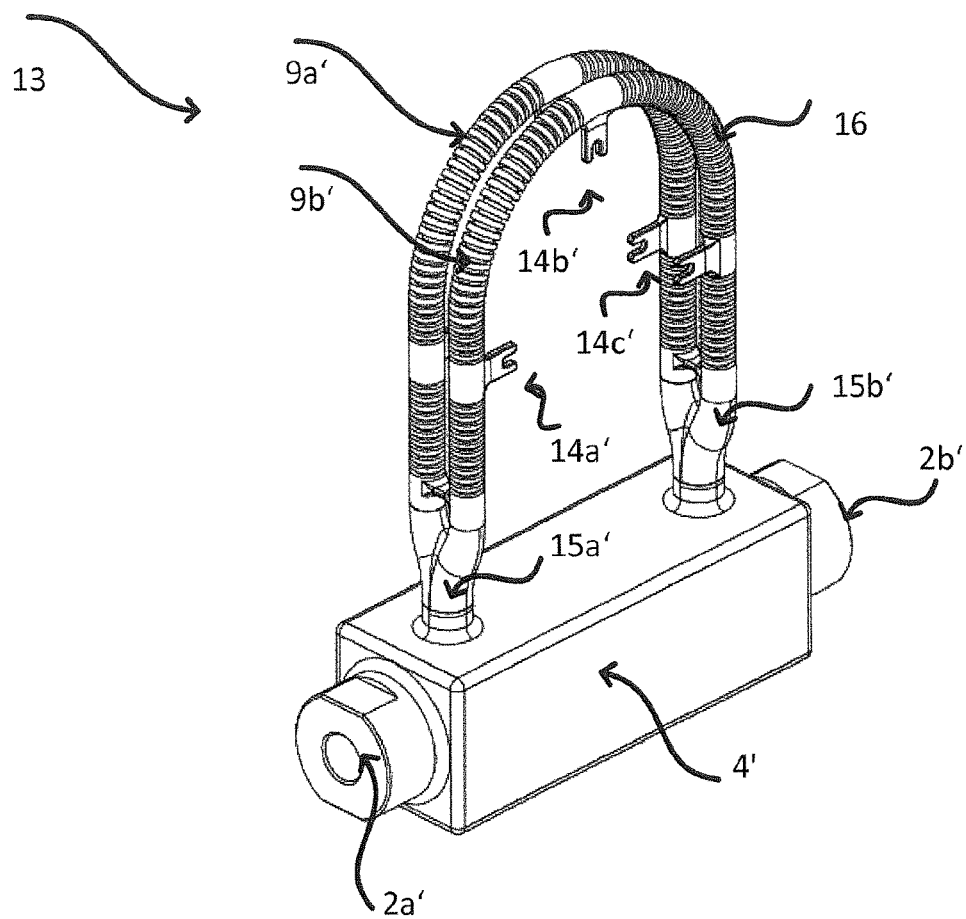
Fig. 2
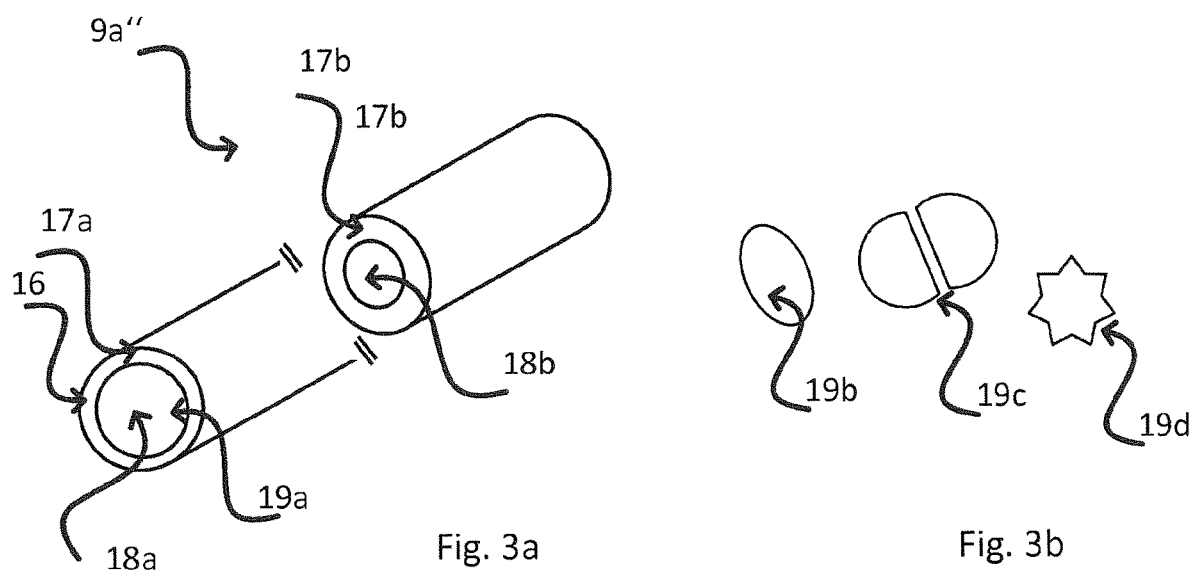
Fig. 3a
Fig. 3b

MEASURING TRANSDUCER OF VIBRATION-TYPE

TECHNICAL FIELD

The present invention relates to a measuring transducer of a vibration-type, especially one for registering and/or monitoring at least one process variable of a flowable medium guided in a pipeline. The process variable can be a physical or chemical process variable, for example, the mass flow of the flowable medium through the pipeline, or, also, the density or the viscosity of the medium. The medium, in turn, can be a gas, a liquid, or a powder, however, also some other flowable material.

BACKGROUND DISCUSSION

Corresponding field devices, especially Coriolis mass flow meters or Coriolis mass flow/densimeters, especially because of their versatility, are widely applied in process and/or automation technology and are manufactured by the company, Endress+Hauser in great diversity and sold, for example, under the mark PROMASS. They are most often integrated as in-line measuring devices in compact construction into the relevant pipeline and have a housing module, which is mechanically coupled with the pipeline via an inlet end and an outlet end. The measuring transducers comprise, furthermore, a sensor module having at least one measuring tube held oscillatably in the housing module, communicating with the pipeline, and executing, at least at times, oscillations, especially bending oscillations, about a static resting position. Furthermore, a measuring device of the field of the invention includes at least one electromechanical, especially electro-dynamic, exciter mechanism acting on the at least one measuring tube for producing and/or maintaining mechanical oscillations of the at least one measuring tube, and at least one vibration sensor arrangement reacting to oscillations of the at least one measuring tube for detecting the oscillations of the at least one measuring tube and for producing at least one oscillatory measurement signal representing oscillations.

The underpinning measuring principles are known from a large number of publications and are described at length and in detail, for example, in U.S. Pat. Nos. 4,793,191, 4,823,614, 4,831,885, 5,602,345, US-A 2007/0151368, US-A 2010/0050783, and published International Applications, WO-A 96/08697, WO-A 2009/120222 and WO-A 2009/120223.

In the course of time, many different embodiments have been proposed and used for the field devices of the field of the invention. Thus, embodiments have been described with 1, 2, 4, or 8 measuring tubes connected in parallel, embodiments, in the case of which the at least one measuring tube is essentially straight, and embodiments, in the case of which the measuring tubes are at least sectionally bent, especially essentially U-, V-, or trapezoidally shaped. The at least one measuring tube is most often manufactured of a metal, especially titanium, zirconium, tantalum or stainless steel, and arranged at least partially within the housing module. For integration of the field device in an existing pipeline, the field device is provided on its in- and outlet ends, in each case, with a process connection, especially a flange.

For field devices with at least two measuring tubes, so-called distributor pieces are provided, one in the region of the inlet end and one in the region of the outlet end process connection. These two distributor pieces are connected mechanically with the housing module, and serve for dividing the flowable medium among the relevant number of measuring tubes, and for the inlet end and the outlet end mechanical connection of the at least two measuring tubes with one another. Additionally, frequently used for field devices with at least two measuring tubes are so-called coupling elements, by means of which the at least two measuring tubes are mechanically coupled at the inlet end and the outlet end.

The coupling elements serve as oscillation nodes.

In contrast, the connecting to the pipeline in the case of field devices with only one measuring tube occurs by means of essentially straight connecting tube pieces, one at the inlet end and one at the outlet end. Furthermore, field devices with only one measuring tube include at least one counteroscillator, which can be embodied as one-piece or a plurality of parts, and which is coupled to the measuring tube for forming inlet end and outlet end coupling zones. In operation of the field device, the counteroscillator either rests, or it is excited to execute oscillations with equal frequency, however, opposite phase, relative to the measuring tube. For example, the counteroscillator can be embodied as an essentially tubular, hollow cylinder, in such a manner that the measuring tube is at least partially jacketed by the counteroscillator.

In operation, the at least one measuring tube is excited to mechanical oscillations in the so-called drive- or wanted mode with the so-called wanted frequency, which is usually a frequency corresponding to an oscillatory mode of the at least one measuring tube, such that the at least one measuring tube executes resonant oscillations. The mechanical oscillations in the wanted mode are, in the most frequently arising case, in which these oscillations correspond to the resonant frequency in the fundamental mode, especially in the case of a Coriolis mass flow- and/or densimeter, as a rule, at least partially embodied as lateral, bending oscillations. In such case, there forms usually in the region of the two ends of the at least one measuring tube, in each case, an oscillation node and in the intermediately lying region exactly one oscillatory antinode. However, also known are applications, in which the torsion mode is excited.

When the medium flows through the at least one measuring tube, there are induced within the measuring tube reaction forces, which lead, in addition to the oscillations in the wanted mode, to equal frequency oscillations in the so-called Coriolis mode, which are superimposed on the oscillations in the wanted mode and, thus, are included in the oscillatory measurement signal. Depending on the type of the induced, and detected, reaction force, various process variables can be registered. For example, the mass flow corresponds to the Coriolis force, the density of the medium to the inertial forces and the viscosity to the friction forces.

The accuracy of measurement, and, partially associated therewith, also the possible application domain, of a field device of the field of the invention of the above described type depend, in such case, on many different factors.

On the one hand, external disturbing influences can negatively influence the accuracy of measurement. These include, for example, vibrations of the pipeline and/or of the housing module, which can couple into the oscillations of the at least one measuring tube. However, also disturbing vibrations from pressure fluctuations of the flowing medium can be problematic, or even different temperature loadings of the different components. Moreover, the accuracy of measurement depends also on how the at least one measuring tube is secured in the housing module. Movements of the end regions of the at least one measuring tube in the housing module can lead, for example, to clamping forces, which act on the process connections and, in given cases, also on the distributor pieces and can lead to deformations of the housing module. It is thus desirable effectively to minimize such and also other, disturbing influences.

For example in this regard, different structural measures relative to the mechanical construction and the connections of the individual components of the particular measuring transducer can be applied. The connections between the at least one measuring tube, the process connections and, in given cases, distributor pieces, as well as the housing module should be as stable and stiff as possible. Moreover, the opportunity for transmission of oscillations from the housing module to the at least one measuring tube should be reduced. It is, however, a fact that many of these measures are accompanied by a marked weight gain, which, in turn, is undesirable, especially in the case of field devices of larger nominal diameter.

On the other hand, the accuracy of measurement depends also on the oscillation characteristics of the at least one measuring tube. Here, special attention should be paid to the frequency spectrum, thus the position of the frequencies of the oscillation modes of the at least one measuring tube. This depends, among other things, on the size, geometry, stiffness, mass distribution and material, of which it is manufactured, as well as, in given cases, on the instantaneous density, viscosity and/or temperature of the respective medium.

An important aspect with reference to an as disturbance free as possible measuring is the relative positions of the frequencies of the oscillation spectra of the at least one measuring tube and the housing module. The oscillation modes of the two components should namely not lie at the same frequencies. Since the resonance frequencies depend basically both on the mass distribution as well as also on the stiffness of the respective components, the positions of the individual oscillation modes can be influenced by variation of these parameters. These measures have, however, structural limits, since certain geometries considered advantageous from the physical standpoint, e.g. certain tube shapes, or radii of curvature, of the at least one measuring tube, are not or only difficultly and/or very complicatedly implementable with established manufacturing processes.

Furthermore, it is desirable for a high accuracy of measurement that the stiffness of the at least one measuring tube be matched to the particular application. For example, the amplitude of the oscillatory measurement signal depends on the stiffness of the measuring tube. Now, it is, however, a fact that a change of the mass distribution changes not only the stiffness but, instead, also the position of the oscillation modes within the oscillation spectrum of the at least one measuring tube. However, it would often be advantageous to vary either only the stiffness at equal remaining frequency spectrum or only the frequency spectrum at equal remaining stiffness. Such requirements can, however, currently only be met with extreme difficulty and/or complications.

SUMMARY OF THE INVENTION

An object of the present invention, therefore, to provide a measuring transducer of vibration-type as well as a method for its manufacture, which measuring transducer is distinguished by an as high as possible accuracy of measurement coupled with as simple as possible manufacture.

This object is achieved according to the invention by a measuring transducer of vibration-type, especially one for registering and/or monitoring at least one process variable of a flowable medium guided in a pipeline, comprising:
a housing module, which is mechanically coupled with the pipeline via an inlet end and an outlet end, and
a sensor module having at least one measuring tube held oscillatably at least partially in the housing module and caused, at least at times, to oscillate,
wherein at least one component of the housing module and/or of the sensor module is manufactured by means of a generative method.

The terminology, a generative, or also additive, manufacturing method, means in the following a method, in the case of which three-dimensional parts are obtained in a primary forming process. A primary forming process is one where a solid body is manufactured from a formless material and the solid body has a defined geometric shape. Generative manufacturing methods, which, in principle, represent an industrialized and mass production capable, further development of so-called "rapid prototyping", are increasingly finding acceptance in industrial manufacturing. A overview concerning the different principles and most current methods is known from a large number of publications.

Common to all generative manufacturing methods is that the desired three-dimensional workpiece is first designed and digitized by computer by means of a model or also freehand using CAD. Then, the workpiece is constructed according to the digital data layer-wise from one or more liquid or solid, especially powdered, raw materials using physical or chemical hardening- or melt-on processes. Typical raw materials are synthetic materials, synthetic resins, ceramics and metals, wherein, depending on applied material, a functional principle appropriate for that material is used.

Generative manufacturing methods offer advantages as follows: On the one hand, the primary forming process clearly reduces material loss compared with a subtractive manufacturing method. Furthermore, the application of generative methods provides time savings, since the parts to be manufactured can be manufactured directly on-site and the production is not limited to the supply of various individual parts. An essential advantage lies, however, in the fact that by means of a regenerative manufacturing method any three-dimensional structure can be designed, and manufactured chipless and/or joint free. Thus, the manufacture of highly complex parts is enabled, which are not manufacturable by means of other manufacturing methods.

Referenced to a measuring transducer of vibration-type, the application of a generative method permits, correspondingly, that individual components can be constructed with previously non-implementable forms, which have special technical advantage. Thus, for example, the embodiment of the measuring tube can be matched optimally to the metrological conditions. Furthermore, the positions of the oscillation modes within the frequency spectrum of the at least one measuring tube can be matched with its stiffness and mass distribution, also with reference to the housing. Moreover, components, which were previously individually manufactured and then assembled, can now be manufactured as one piece. This increases, in given cases, stability and reduces the occurrence of disturbing influences due to unwanted vibrations. Moreover, mounting times are accelerated.

Advantageously, the measuring transducer includes, furthermore,
at least one electromechanical, especially electro-dynamic, exciter mechanism acting on the at least one measuring tube for producing and/or maintaining mechanical oscillations of the at least one measuring tube, at least one vibration sensor arrangement reacting to oscillations of the at least one measuring tube for producing at least one oscillatory measurement signal representing oscillations of the at least one measuring tube, wherein the at least one exciter mechanism and the at least one vibration sensor arrangement are secured externally to the at least one measuring tube.

The at least one component manufactured by means of a generative method is, for example, the at least one measuring tube or the housing module. It can either be an individual component manufactured in this way or at least two components manufactured together as one piece. The latter saves especially at least one step in the assembly of the measuring transducer. Also, a joint free connection of two parts is usually especially stable and stiff, which is likewise an advantage.

The present invention permits a large number of embodiments, of which some form subject matter of the dependent claims. Some embodiments can be applied to a large number of different components, while some concern individual, specific components, for which component specific requirements should be fulfilled. It should be noted that the examples covered here represent no exclusive listing of the possible structures of embodiment, but, rather, that besides those presented here a large number of further options will be apparent, which all likewise fall within the scope of the present invention.

Independently of which component it happens to be, a higher level goal is a targeted influencing of the stiffness of the component. This holds especially for the at least one measuring tube, however, also for the housing module. The application of a generative manufacturing process with the above set-forth advantages opens innumerable new options, of which some will now be discussed.

Targeted, especially also anisotropic, influencing of the stiffness of at least one component of a measuring transducer of vibration-type can lead, for example, depending on component, to the following advantageous effects: As regards the construction of the at least one measuring tube, with positions of the oscillation modes remaining constant, an as small as possible stiffness can be achieved, which can lead to a larger oscillatory measurement signal and, associated therewith, a higher accuracy of measurement. Especially, the stiffness can be position specifically increased or lessened in such a manner that it is fitted to the wanted mode along the measuring tube in regions of oscillation antinodes differently than in regions with oscillation nodes, which likewise can be advantageous for measuring performance.

Similarly, it can be advantageous for the housing module, when the stiffness is greater in regions, in which the forces acting on the housing are especially large, such as, for example, in the region of the connection of the housing module with the process connections and, in given cases, with the distributor pieces, than in other regions, which are not exposed to large forces. In such case, however, especially in the case of large nominal diameters, the mass of the housing module should not or only slightly be increased compared with a conventional embodiment, since the empty weights of field devices of the field of the invention with large nominal diameters are, in any event already very high, for instance in the range of a number of hundred kilograms. Furthermore, in the case of the housing module, the position of the frequency of the fundamental oscillation mode rises with increasing stiffness, so that by varying the stiffness the position of the oscillation modes of the frequency spectrum of the housing module can, with targeting, be separated from those of the at least one measuring tube.

In an embodiment of a measuring transducer of the invention, the wall thickness, and/or the stiffness, and/or the mass distribution and/or the density of the at least one component vary, especially heterogeneously, in the direction parallel to the flow direction of the medium. In this way, it can be achieved that the at least one measuring tube has sectionally different stiffnesses.

Another embodiment of the invention includes the provision that the wall of the at least one component has, at least externally, at least in a portion, a profile, especially a groove profile, a jagged profile or a tooth profile. Also by through these measures, the stiffness of the at least one component can be influenced toward the achievement of desired goals. In such case, it is, depending on component of the measurement transducer, even possible to provide the wall with a corrugation, as well as also to integrate openings/hollow spaces within the wall.

A further higher-level goal lies in the reduction of incoupled, disturbing influences, especially those from unwanted vibrations. The occurrence of such influences can basically not be avoided, since the particular field device is, as a rule, integrated in an existing pipeline and connected with such mechanically solidly and sealedly. Therefore, it is advantageous to design individual components of the measuring transducer, especially with reference to the geometry and/or choice of material, in such a manner that they damp in-coupled oscillations and/or other disturbing influences.

In an especially preferred embodiment, there is, therefore, integrated within the wall of the at least one component at least one capsule enclosing powder, and/or at least one hollow space. The inclusion of powder filled capsules and/or hollow spaces into the wall of the at least one component offers especially the damping of unwanted vibrations, as well as also other disturbing influences.

This measure can especially be implemented toward the achievement of desired goals only by means of a generative method. Fundamentally, during the layered construction of the at least one component, for example, the applied raw material, especially a powder, is not hardened in individual, smaller, correspondingly selected regions, the capsules. During the hardening of the respective component, the particular raw material is then locked into the specially selected regions.

Another embodiment for reducing disturbing influences provides that there is integrated within the wall of the at least one component at least one hollow duct or in at least one portion within the wall an open pored structure, especially a porous structure or a beehive structure. Again, the implementing of such a solution without a generative manufacturing method is only very difficultly or even not possible.

It is advantageous when the at least one measuring tube is manufactured by means of the generative method. The application of such a method enables a large number of new, advantageous embodiments, which clearly go beyond the advantageous properties of conventional measuring tubes. Especially, a large number of previously non-implementable geometries become possible, which bring great technical advantages. For the at least one measuring tube as oscillatable unit of the field device, an intelligent choice of geometries and materials with reference to the resulting oscillation characteristics can determine the achievable accuracy of measurement in high degree.

Some examples of advantageous embodiments of the at least one measuring tube, which are for the most part only sensibly manufacturable by application of a generative method, will now be presented in the following, wherein it is noted that this is not an exclusive listing.

In an embodiment, at least one connecting piece for securement of at least one component of the exciter mechanism and/or vibration sensor arrangement is placed externally of the wall of the at least one measuring tube, wherein the at least one connecting piece and the wall of the at least one measuring tube are manufactured together by means of the generative method. The manufacture of a measuring tube without the need for additional add-on parts for securement of further components, on the one hand, saves time in the assembly of the field device. On the other hand, there results a direct manufacture of the measuring tube with the corresponding connecting pieces joint freely in one piece in a clearly stronger and more stable connection. This can be advantageous especially with reference to vibrations.

In an embodiment, the cross sectional area of the at least one measuring tube is round, star-shaped, square, oval, or circular segment shaped, especially D-shaped, and/or the cross sectional area of the at least one measuring tube varies in the direction parallel to the flow direction of the medium with reference to surface area and surface form. Different geometries result in different stiffnesses of the measuring tube. For example, a star-shaped geometry has a smaller stiffness compared with a round cross sectional area, so that the position of the resonant frequency of the fundamental oscillation mode sinks. Therewith, a greater accuracy can be achieved as regards determining the viscosity. A circular segment shaped cross section provides, for example, supplementally, a space saving. Moreover, certain geometries are more advantageous than others for exciting special oscillation modes, such as, for example, the torsion mode.

In an embodiment, there is integrated in the interior of the wall of the at least one measuring tube at least one flow forming module, especially introduced into the inner wall surface, a lamella, a flow rectifier or a filter, or at least one partition, which divides the internal volume into at least two regions, wherein the wall of the at least one measuring tube and the at least one flow forming module are manufactured together by means of the generative method. Thus, disturbing influences brought about by the flow can be minimized. Partitions introduce, for example, depending on application, a space saving. Furthermore, especially a division of the individual tubes into a number of subtubes changes the stiffness between the empty pipe and the pipe flowed-through by medium. In this way, likewise disturbance effects, which occur from the flowing medium, especially by the mass of the medium moved by the oscillations of the measuring tube, are reduced.

Moreover, it is advantageous, when the wall thickness of the at least one measuring tube is greater in regions, in which the deflection of the at least one measuring tube is maximum when it executes mechanical oscillations in the first and/or second oscillatory mode, than in regions, in which nodes of the first and/or second oscillatory mode are present.

In an embodiment, the measuring transducer includes at least one bypass line, through which a portion of the flowing medium flows, wherein the wall of the at least one measuring tube and the at least one bypass line are manufactured together by means of the generative method. Then integrated in the bypass line can be, for example, a further sensor for registering an additional process variable, for example, the temperature.

An embodiment provides that there is arranged in the interior of the wall of the at least one measuring tube at least one structure, especially a strut or a band, which structure is secured to two contact areas on the inner wall of the at least one measuring tube. These have a stabilizing effect, in such a manner that the at least one measuring tube does not warp or warps less in the case of a medium flowing under pressure.

In an embodiment, the at least one measuring tube is at least sectionally significantly curved, especially embodied in U-, V-, trapezoid-, or helical-shape. Generative methods permit in this regard previously not possible radii of curvature of the measuring tube, however, also completely new bending arrangements, such as helically shaped, or screw shaped measuring tubes.

An embodiment includes that externally on the wall of the at least one measuring tube at least one mass element is arranged, which is secured by means of at least one securement unit, especially a strut extending parallel or perpendicular to the flow direction of the medium, a ring extending radially around the wall of the at least one measuring tube, or a fin extending along the wall of the at least one measuring tube parallel to the flow direction, in such a manner that at least one of the two contact areas between the at least one securement unit and the at least one mass element and/or the at least one securement unit and the external region of the wall of the at least one measuring tube is minimal, and wherein the at least one measuring tube, the at least one mass element, and the at least one securement unit are manufactured together by means of the generative method. In this way, the mass distribution is changed, or increased, by the adding of at least one mass element, whereby the position of the oscillation modes within the frequency spectrum, thus the frequencies, which excite certain oscillation modes, is changed. Advantageously, however, these measures only minimally change the stiffness of the at least one measuring tube, since the contact areas between the at least one securement unit and the at least one measuring tube are minimized. Thus, variables otherwise dependent on one another can be varied independently of one another by means of a construction corresponding to this embodiment. Distributions of the mass elements can be both symmetric as well as also asymmetric, wherein the arrangement can be matched goal oriented to the particularly desired properties. Correspondingly, this embodiment permits a large number of possible geometries, which all fall within the scope of the present invention.

In an embodiment, at least two fins are placed externally on the wall of the at least one measuring tube on oppositely lying sides of the at least one measuring tube, wherein the at least one measuring tube and the at least two fins are manufactured together by means of the generative method. This measure brings about a directional dependence of the stiffness. Since the oscillatory movements of the at least one measuring tube are different in different directions, then the stiffness of the measuring tube can be different for different oscillation modes.

In an embodiment, the sensor module of the measuring transducer includes at least
  a single measuring tube, and
  two process connections,
wherein the measuring tube and at least one of the two process connections are manufactured together by means of the generative method. This brings anew advantages in the stability and stiffness of the connections of the different components as well as in the mounting. In such case, it is advantageous, when, such as above mentioned, a vibration absorbing tube is provided to serve as a counteroscillator, wherein the vibration absorbing tube and the at least one measuring tube are manufactured together by means of the generative method. In such case, many different geometries can be considered for the geometry of the vibration absorbing tube. Advantageously, the vibration absorbing tube has, for example, a greater diameter than the measuring tube, wherein the measuring tube is arranged coaxially, especially contactlessly, in the interior of the vibration absorbing tube.

In an alternative embodiment, the sensor module of the measuring transducer includes at least,
   at least two measuring tubes,
   two distributor pieces, which distribute the medium flowing from the pipeline into the inlet ends of the at least two measuring tubes and bring the flowing medium back together at the outlet ends of the at least two measuring tubes, and thus connect the pipeline and the at least two measuring tubes, and
   two process connections,
wherein the at least two measuring tubes and at least one of the distributor pieces or the at least two measuring tubes, the two distributor pieces and at least one of the process connections are manufactured together by means of the generative method. Resulting for these embodiments are the same advantages as for the above embodiments with a single measuring tube. In the case of a measuring transducer with at least two measuring tubes, it is, furthermore, advantageous, when at least two coupling elements, such as likewise mentioned above, are provided, which couple the at least two measuring tubes with one another at least at the inlet end and at the outlet end, wherein the at least two measuring tubes and the at least two coupling elements are manufactured together by means of the generative method.

Moreover, it is advantageous when in the case of a measuring transducer with at least two measuring tubes each of the two distributor pieces has a multiply branched, continuous, internal volume. In this way, the flow behavior can be optimized. Moreover, this type of distributor pieces permits the application of the measuring transducer in a branched line with central flow measurement.

Special embodiments with advantageous effects result likewise for the housing module. Correspondingly, in one embodiment, at least one component of the housing module is manufactured by means of the generative method. Also to be noted here is that the following number of embodiments discussed is in no case complete. Rather, numerous other variants fall within the scope of the present invention.

In one embodiment, a filling, especially a filling with a porous structure or beehive structure, is arranged in at least a part of the interior of at least one component of the housing module. The filling is either introduced subsequently into the at least one component of the housing module, or the filling and the at least one component of the housing module are manufactured together by means of the generative method. The filling acts as an oscillation damper with reference to unwanted vibrations and/or external, disturbing influences. Moreover, if one selects a filler, which already has good oscillation damping properties at very small density, then it can be achieved that the weight of the housing module is not or only slightly increased, a feature which especially brings a considerable advantage in the case of field devices of larger nominal diameters.

Another embodiment provides that at least one component of an electronics unit, especially a housing, at least one electrical feedthrough and/or a mechanical transition piece, especially for an Ex-protection feedthrough, is manufactured together with at least one component of the housing module by means of the generative method. This brings both advantages with reference to the assembly, as well as also with reference to the stability of the securement of the component on or in the measuring transducer.

In an embodiment, the housing module includes a support, with which the at least one measuring tube is mechanically connected inlet end and outlet end, and a casing, which surrounds the at least one measuring tube. Then it is advantageous, when at least the support and/or at least one of the process connections and/or at least one of the distributor pieces are manufactured together by means of the generative method. Furthermore, it is advantageous, when the support is embodied as a laterally at least partially open, especially tubular, support cylinder, which is connected with the at least one measuring tube in such a manner that the at least one measuring tube protrudes partially laterally out of the support cylinder.

Another embodiment provides that at least one other sensor element is integrated in at least one of the subcomponents of the housing module and/or sensor module for registering an additional process variable, especially temperature or pressure, wherein the at least one component of the housing module or sensor module and at least one component of the other sensor element are manufactured together by means of the generative method.

Of course, also a number of the here mentioned embodiments can be combined with one another, in order to increase the accuracy of measurement of the measuring transducer. It is also an option that at least all mechanical components of a measuring transducer are manufactured together by means of the generative method.

For a measuring transducer of the invention, it is, furthermore, advantageous when at least one component of the housing module and/or of the sensor module is manufactured of a metal, especially stainless steel or tantalum, a composite material, especially a fiber composite material, a glass or a synthetic material, e.g. a plastic. However, also other materials can be advantageously used. At least process contacting components are frequently matched to the existing pipelines, into which the measuring transducer is to be integrated.

Advantageously, moreover, a coating is applied on at least one portion of at least one surface of at least one component of the housing module and/or of the sensor module, especially for preventing corrosion, abrasion and/or accretion formation. Especially, the coating is melted or welded on.

Another embodiment provides, finally, that the at least one process variable is the mass flow, the density, or the viscosity of the medium.

The object of the invention is likewise achieved by a method for manufacturing at least one component of a measuring transducer of vibration-type, especially for registering and/or monitoring at least one process variable of a flowable medium guided in a pipeline, especially a measuring transducer according to one of the preceding claims, which measuring transducer at least includes:
   a housing module,
      which is designed to be coupled mechanically with the pipeline via an inlet end and an outlet end, and
   a sensor module having at least one measuring tube held oscillatably in the housing module and caused to oscillate, at least at times,
wherein at least one component is manufactured in a primary forming process, especially by means of a layered applying and/or melting-on of a liquid or solid material, especially a powdered material, especially a metal powder, based on a digital data set, which gives at least the shape and/or the material and/or the structure of the at least one component. The at least one component is thus manufactured according to the invention by means of a generative method.

As above already described, the application of a generative manufacturing method opens especially new advantageous options for forming and embodiment of workpieces manufactured by means of this method. Individual or a number of components of a measuring transducer can be manufactured by means of such a method. Besides a simplified, time- and material saving manner of manufacture, which can, moreover, also take place directly at the customer's plant, the character of the particular component can be optimized with reference to diverse, metrologically relevant, physical relationships. Some examples of metrologically or otherwise advantageous conditions regarding the construction of a component of a measuring transducer of the invention will now be explored as follows. It is understood, however, that, depending on application and the requirements on the measuring transducer associated therewith, it can likewise be expedient, to set up other conditions and to take such into consideration.

In an embodiment of the method of the invention, for determining the shape and/or structure and/or the material of the at least one component, the geometry, mass distribution, and/or stiffness of the at least one component is set in such a manner, especially by means of an iterative simulation, especially a finite elements simulation, that a predeterminable condition is fulfilled.

Since in the case of the application of a generative manufacturing method, the workpiece to be manufactured is first designed and digitized per computer by means of a model or even freely per CAD, varied options result for optimizing the forming and the materials. On the one hand, analytically or also empirically determined criteria can be given in the form of equations and/or formulas, which are to be taken into consideration in the design. However, also simulation methods, especially iterative simulation methods, such as, for example, the so-called finite elements method, can be used, in order to optimize the forming of the workpiece as regards its different characteristic variables, such as, for example, its density, mass, stiffness, and/or geometry. Because the component is first digitally created, significant time can be saved in the finding of the optimal geometry.

An embodiment provides that the stiffness of the at least one component is kept constant, while at least one frequency corresponding to one of the oscillation modes of the at least one component is set to a predeterminable value. As already described, especially the resonant frequency of the fundamental oscillation mode depends on the stiffness and the mass, especially the mass distribution, of the component. In order to hold the stiffness constant and to set the frequency, the mass, i.e. the mass distribution, must be changed in such a manner that the stiffness is not simultaneously changed. Helpful here is the described method, for example, especially in combination with the embodiment of the measuring transducer, in which the integration of additional mass elements is provided. Since, in the case of the embodiment of the at least one measuring tube containing the mass elements, the contact areas between possible connecting pieces for securing the mass elements to the measuring tube are kept minimal, the stiffness remains correspondingly essentially unchanged.

Conversely, another variant of the method of the invention provides that at least one frequency corresponding to one of the oscillation modes of the at least one component is kept constant, while at least the stiffness is set to a predeterminable value. In such case, the stiffness can be anisotropically changed, or even increased or lessened over the entire measuring tube. Which variant is helpful depends on the metrological requirements of the particular application for the measuring transducer.

An embodiment provides, furthermore, that the mass distribution, stiffness and/or geometry of the at least one component is selected in such a manner that at least one frequency corresponding to one of the oscillation modes of the housing module and at least one frequency corresponding to one of the oscillation modes of the sensor module are different from one another. Here, either one or more components of the housing module, one or more components of the sensor module or also at least one component of the housing module and one component of the sensor module can simultaneously be optimized and matched to one another, in order to achieve an as good as possible decoupling over a frequency interval containing all metrologically relevant oscillation modes. This clearly reduces the in-coupling of disturbing vibrations of the housing into the oscillatory measurement signal.

In an embodiment, the at least one component is the at least one measuring tube flowed through by the fluid, wherein the geometry, stiffness and/or mass distribution of the at least one measuring tube are/is selected in such a manner that the flow profile is conditioned and at least one disturbance effect evoked by the flow of the medium is minimized. This can be brought about, for example, by flow forming modules described in connection with another embodiment. However, also other measures, such as specially embodied distributor pieces, variable cross-sectional areas of the at least one measuring tube or the like can be suitable for influencing the flow profile. Which measure is best in which case depends on the character of the particular flowable medium and the particular application of the measuring transducer.

It is advantageous, when the primary forming process for manufacturing the at least one component is selective laser sintering, selective laser melting, laser deposition welding, a metal powder application method, fused deposition modeling, multi-jet modeling, color jet printing, or LaserCUSING. These are some of the established generative manufacturing methods.

As above described, generative manufacturing methods operate essentially based on so-called rapid prototyping (rapid model making). Correspondingly, the concept, rapid prototyping, is sometimes also used as a generic terminology for different manufacturing methods for fast manufacture of sample workpieces based on digital construction data, in the case of which electronic data of a three dimensional model of the workpiece are converted directly and rapidly into a physical product as much as possible without manual detours or forms. All methods known under this concept have in common that the particular workpiece is constructed layer-wise from formless or form neutral, raw material using physical and/or chemical effects.

In the case of fused deposition modeling (melt coating), a workpiece is constructed layer-wise from a meltable plastic, wherein the individual layers connect to form a manufactured workpiece. Machines for melt coating belong to the machine class of 3D-printers. The method is based on the liquefying of a wire shaped plastic or wax material by heating. During subsequent cooling, the raw material solidifies. The raw material deposition occurs by extrusion with an heating jet freely displaceable in the manufacturing plane.

In the case of multi-jet modeling, the workpiece is layer-wise constructed by a pressure head having a number of linearly arranged nozzles, which function similarly to the pressure head of an ink jet printer. Corresponding machines suitable for this method belong usually likewise to the machine class of the 3D-printer. Due to the small size of the droplets formed during the method, also fine details can be provided in a workpiece. Suited as raw material are, for example, UV-sensitive photopolymers. These raw materials in the form of monomers are polymerized by means of UV-light directly after the "printing" onto already present layers and, in such case, transformed from the liquid starting state into the solid end state.

Selective laser sintering is a method, in the case of which a workpiece is manufactured by a sinter process layer-wise from a powdered starting material, especially a polyamide, another plastic, a plastic coated molding sand, or a metal- or ceramic powder. Also here, 3D-printing presses are again frequently used. The powder is applied flushly on a construction platform with the assistance of a doctor blade or roller. The layers are step-wise sintered or melted into place in the powder bed by a position selective radiation of light by means of a laser, especially a CO2 laser, a Nd:YAG laser or a fiber laser, in accordance with the layer contour of the component. The construction platform is then slightly lowered and a new layer coated. The powder is provided by lifting a powder platform or as a supply in the doctor blade. The processing occurs layer by layer in the vertical direction. The energy, which is fed by the laser, is absorbed by the powder and leads to a locally limited sintering or melting of particles with reduction of the total surface area. In this way, any three-dimensional workpiece can be manufactured, especially workpieces, which cannot be manufactured by means of conventional mechanical or casting manufacturing methods.

Fundamentally in the case of the laser-based methods, different method variants are distinguished. In the case of the classic variant, the powder grains are only partially melted and a liquid phase sinter process occurs. This variant is applied in the case of the sintering of plastic material and partially in the case of the sintering of metal with special sinter powder. An option is, however, also the direct application of metal powder without addition of a binder. The metal powders are, in such case, completely melted. For such purpose, as a rule, CW lasers are applied. This method variant is also referred to as selective laser melting (SLM).

Laser deposition welding is, in turn, a type of cladding (deposition welding), in the case of which surface deposition occurs on a workpiece by means of melting and simultaneous application of almost any raw material. This can happen in powder form e.g. as metal powder or also with a welding wire, respectively—tape. In the case of laser deposition welding, the heat source is a laser of high power, principally diode lasers or fiber lasers, earlier also CO2- and Nd:YAG lasers. In the case of laser deposition welding with powder, the laser heats the workpiece, most often, defocused, and melts it locally. At the same time, an inert gas mixed with fine metal powder is fed. The supplying of the working region with the metal/gas mixture occurs via trailer- or coaxial nozzles. At the heated location, the metal powder melts and connects with the metal of the workpiece. Besides metal powder, also ceramic powder materials, and special hard materials, can be used. Laser deposition welding with wire or tape functions analogously to the method with powder, however, with wire or tape as the additive material.

An especially preferred manufacturing process is the so-called LaserCUSING, which was, is being, developed by the firm, CONCEPTLASER of the Hofmann Innovation Group. In such case, involved is a melt method, in the case of which a workpiece is generated layer-wise using 3D CAD data. The special feature is that a stochastic lighting strategy is applied, so that each layer is executed segment-wise and successively. This provides a significant reduction of stresses in the resulting workpiece.

For workpieces of plastic, also so-called plastic freeforming represents an option, in the case of which a so called freeformer is used. The freeformer melts plastic granulate such as in the case of injection molding and produces liquid melt droplets, from which, additively—thus layer upon layer—the containment is built up. Therewith, individual parts manufacture is performed based on 3D-CAD data without any need for injection molding tooling. The raw material preparation functions, in principle, as in the case of injection molding. The granular material is filled into the machine. A heated plastifier cylinder leads the plastic melt to a deposition unit. Its jet closure enables with high-frequency piezotechnology fast opening- and closing movements and so produces under pressure the plastic droplets, from which the plastic part builds additively dust- and emission freely. In the case of the freeformer, however, the deposition unit keeps its nozzle exactly in the vertical position. Instead, the component support moves. Besides a component support serially movable via three axes, optionally a variant with five axes is available. Since the device has two deposition units, two raw materials or colors can be processed together.

This discussion of generative methods is, in no way, exhaustive. Rather, some of the established and advantageously usable methods have been listed by way of example.

In the case of an additional method of the invention, the digital data set, which gives at least the shape and/or the material and/or the structure of the at least one component, is transmitted to the customer, and the at least one component is manufactured on-site at the customer's location by means of a primary forming process. If the customer has a corresponding machine enabling performance of the particular generative method, then, in this way, time and also storage costs can be saved. Solely the digital data set, which describes the particular component, must be electronically transmitted. This is especially advantageous for special cases, where only a small number of pieces need to be manufactured.

A measuring transducer of the invention is especially advantageously applied in the case of a measuring device for registering and/or monitoring at least one process variable of a medium guided flowably in a pipeline. Examples of such a device include a Coriolis mass flow meter or Coriolis mass flow/densimeter.

BRIEF DESCRIPTION OF THE DRAWINGS

The invention will now be described in greater detail based on the appended drawing, FIGS. 1 to 9 of which show as follows:

FIG. 2 is a first embodiment of the invention with two measuring tubes;

FIG. 3 is a measuring tube of the invention (a) with variable wall thickness and cross sectional area and (b) with different options for the cross sectional shape;

DETAILED DISCUSSION IN CONJUNCTION WITH THE DRAWINGS

Figure 1A:
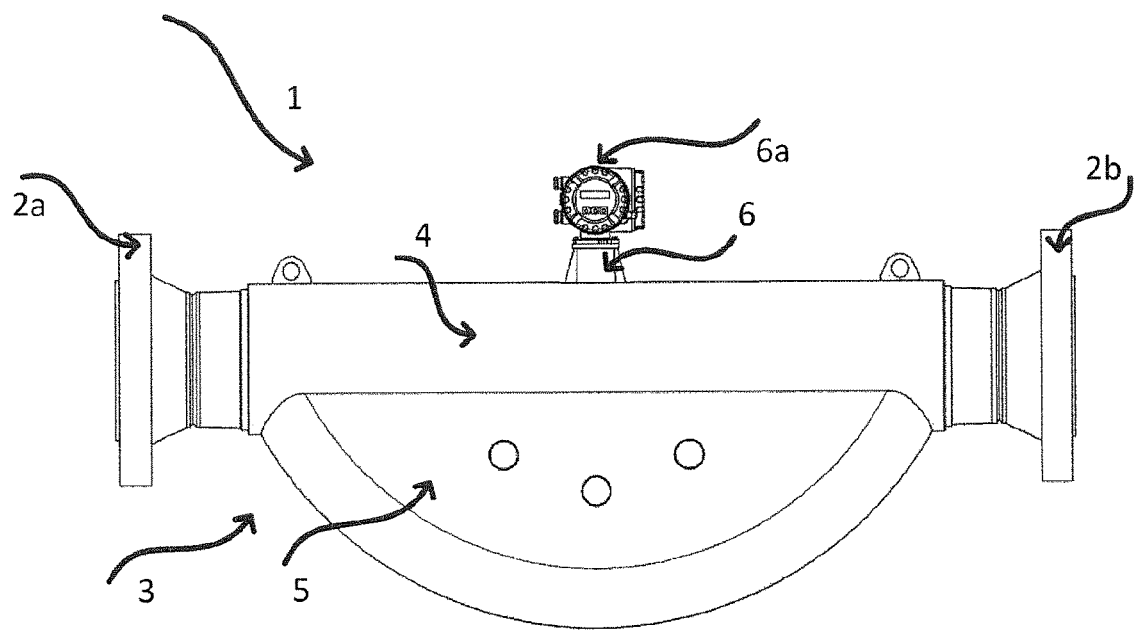
FIG. 1 is a field device of the state of the art of the field of the invention with two measuring tubes and a housing module with a support and a casing (a) in a sectional illustration, (b) in a perspective and exploded view and (c) in a sectional illustration without housing module.
Figure 1B:
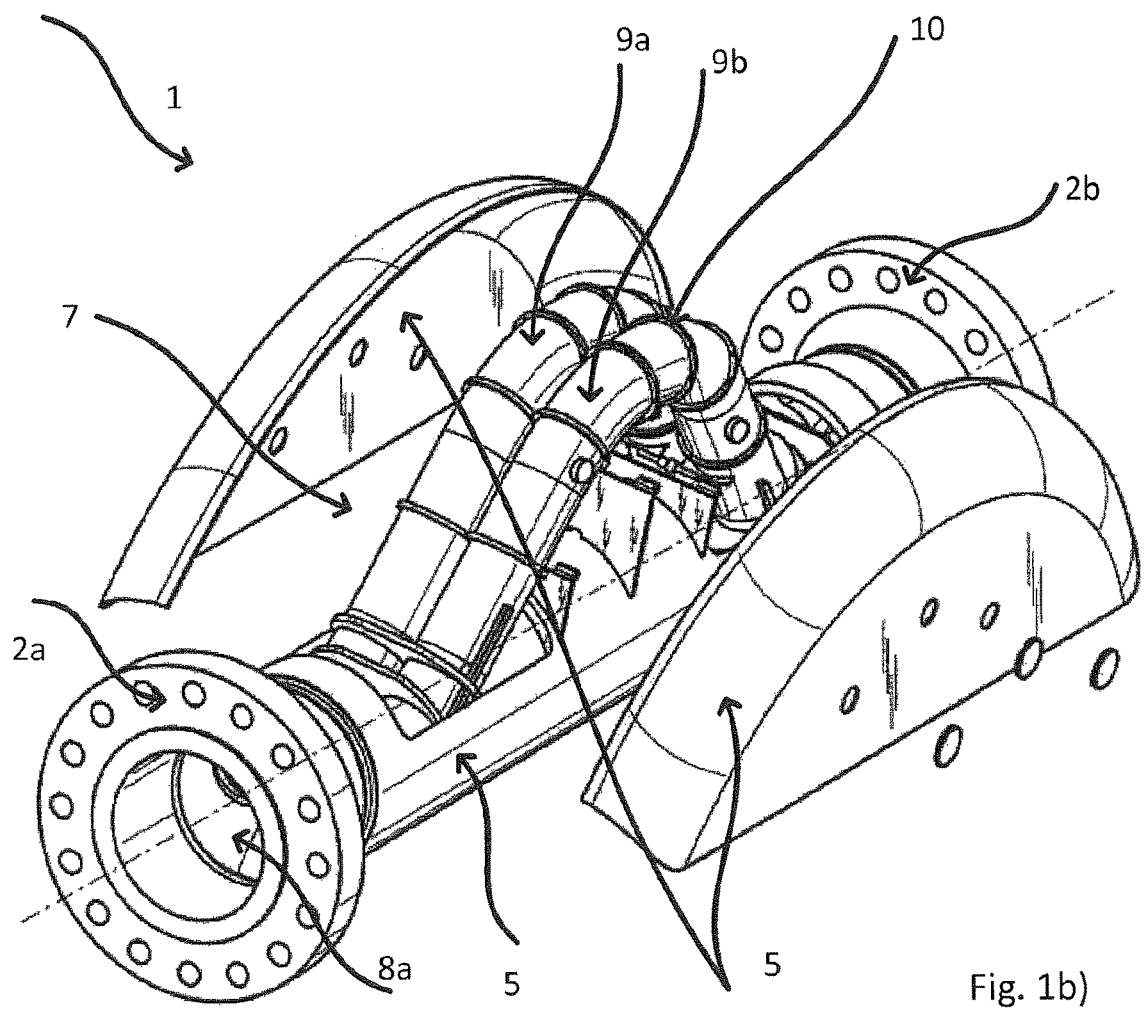
Figure 1C:
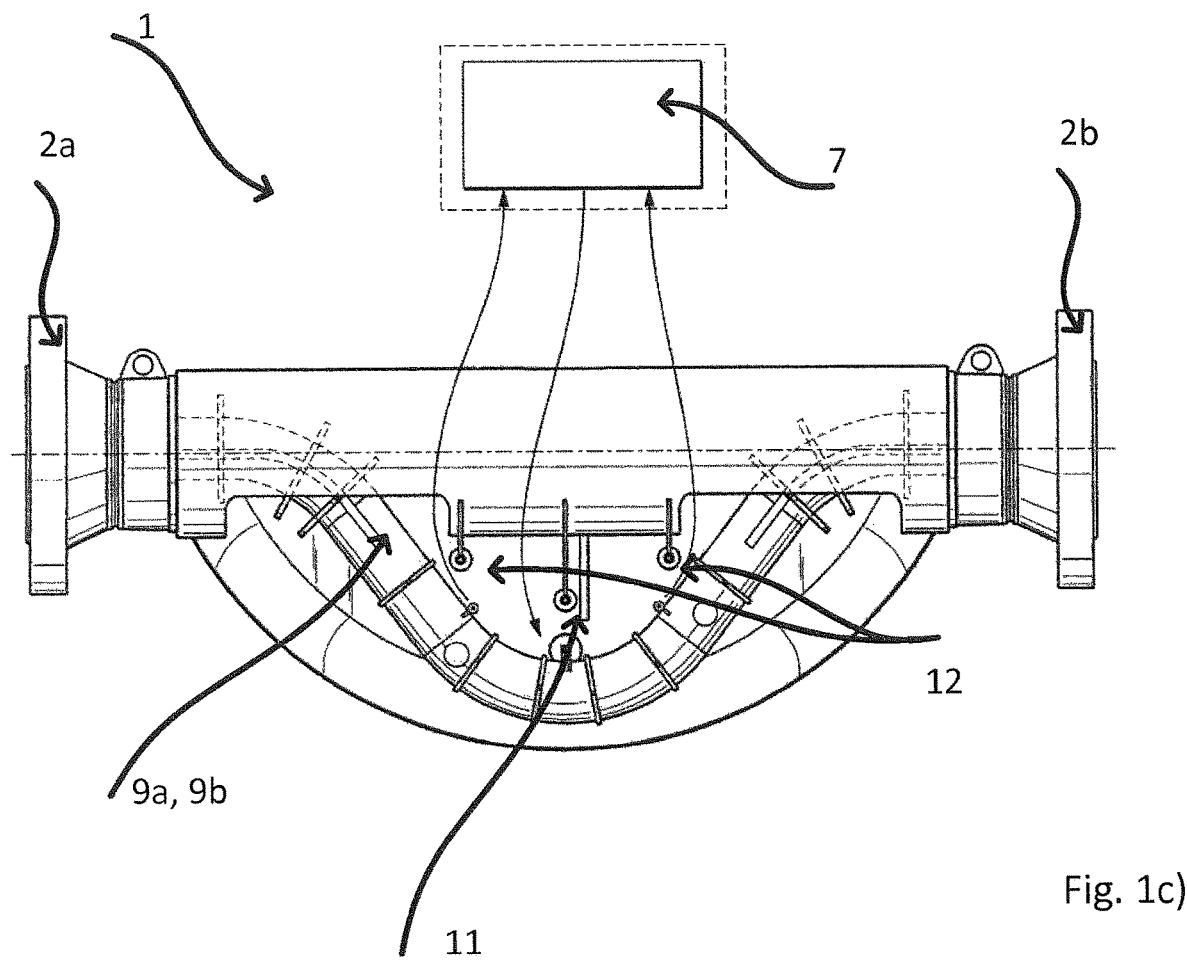

FIG. 1 shows, by way of example, a field device 1 of the field of the invention according to the state of the art with two measuring tubes 9a,9b and a housing module 3 with support 4 and casing 5. In such case, FIG. 1a is an external view, while FIGS. 1b and 1c show interior views of the same field device 1.

FIG. 1a shows an inlet end process connection 2a and an outlet end process connection 2b, by means of which the field device 1 can be integrated into an existing pipeline (not shown). Furthermore, the housing module 3 is visible, which in the embodiment shown here is composed of a support 4 in the form of a laterally at least partially open support cylinder, especially a tubular support cylinder, which is connected with the two measuring tubes (9a,9b; compare FIG. 1b), and a casing 5 surrounding at least the two measuring tubes 9a,9b and secured to the support 4. Mounted on the support 4 is, furthermore, a neck tube 6, via which an electronics unit 6a can be connected, which serves, for example, for signal registration, evaluation, and feeding.

The internal construction and especially the sensor module 7 of the field device 1 is better visible in the perspective representation in FIG. 1b. Integrated in the region of the inlet end process connection 2a and outlet end process connection 2b are an inlet end distributor piece 8a and an outlet end distributor piece 8b (not visible, see FIG. 1c), which distributor pieces 8a,8b are mechanically connected with the support 5 (not visible in this view). The stability of these connections is of great importance for the accuracy of measurement of the field device 1. The distributor pieces 8a,8b are likewise connected with the two measuring tubes 9a,9b and distribute and return the flowing medium respectively from and to the pipeline (not shown).

The two measuring tubes 9a, 9b, which at inlet end and outlet end extend out from the support 5, are mechanically coupled with one another by means of a number of coupling elements 10 (the lead line points to only one coupling element; there are, however, along the measuring tube a number of equivalent elements, which for reasons of perspicuity have not been provided with additional lead lines).

Other details of the construction are, finally, to be understood from the sectional illustration in FIG. 1c. Each of the two measuring tubes 9a,9b executes, during operation, oscillations, whose one possible movement track is indicated in the figure. Furthermore, at least one electromechanical, especially electro-dynamic, exciter mechanism 11 is shown acting on at least one measuring tube 9a,9b for producing and/or maintaining mechanical oscillations of the at least one measuring tube 9a,9b, as well as at least one vibration sensor arrangement 12 reacting to oscillations of the at least one measuring tube 9a,9b for producing at least one oscillatory measurement signal representing oscillations of the at least one measuring tube.

FIG. 2 shows a first embodiment of a measuring transducer 13 of the invention. For purposes of simplification, the exciter mechanism 11 as well as vibration sensor arrangement 12 are not shown. Measuring transducer 13 includes two measuring tubes 9a',9b', which together with a support 4', two process connections 2a', 2b' and two distributor pieces 15a', 15b' are manufactured as one piece. Additionally visible for securement of an exciter mechanism 11 and vibration sensor arrangement 12 are six, pairwise arranged, connecting pieces, which likewise are manufactured with the above mentioned components as one piece. The walls of the two measuring tubes 9a',9b' have a profile, here a groove profile 16.

FIG. 3 shows other embodiments of the invention for a measuring tube 9a'', which, by way of example, is a straight tube. As evident from FIG. 3a, the wall thickness 17a, 17b of the measuring tube 9a'', i.e. the thickness of the wall 16, can vary along the length of the measuring tube 9a''. In this example, in a first subsection, the wall thickness 17a is less than the wall thickness 17b in a second subsection. Correspondingly, the cross sectional area 18a of the measuring tube 9a'' is greater in the first subsection than the cross sectional area 18b in the second subsection. Cross sectional area is, in such case, the area, which is surrounded by the wall 16 and whose normal vector points in the direction of the longitudinal axis of the measuring tube 9a''. The longitudinal axis extends parallel to the flow direction of the respective medium.

Besides a variable wall thickness 17a,17b', and a variable cross sectional area 18a,18b, also the cross sectional shape 19a-d'' can be varied, meaning in the following that the geometry of the cross sectional area 18a,18b can be varied. While the cross sectional shape 19a for measuring tube 9a'' in FIG. 3a is round in both subsections, are other possible cross-sectional shapes 19b-d are shown in FIG. 3b, in each case without drawing the complete measuring tube 9a''. Examples include an oval 19b, a star-shaped 19d, and a circular segment shaped 19c cross sectional shape. The choice of a circular segment shaped, cross sectional shape 19c is, among other things, advantageous with reference to the space saving associated therewith in the case of application of more than one measuring tube 9a'',9b'', which results from the opportunity to position the at least two measuring tubes 9a'', 9b'' next to one another in such a manner that the straight regions of the peripheries adjoin one another.

Such geometric embodiments of a measuring tube 9a'', 9b'' are not or only very difficultly implementable with conventional methods.

Figure 4A:
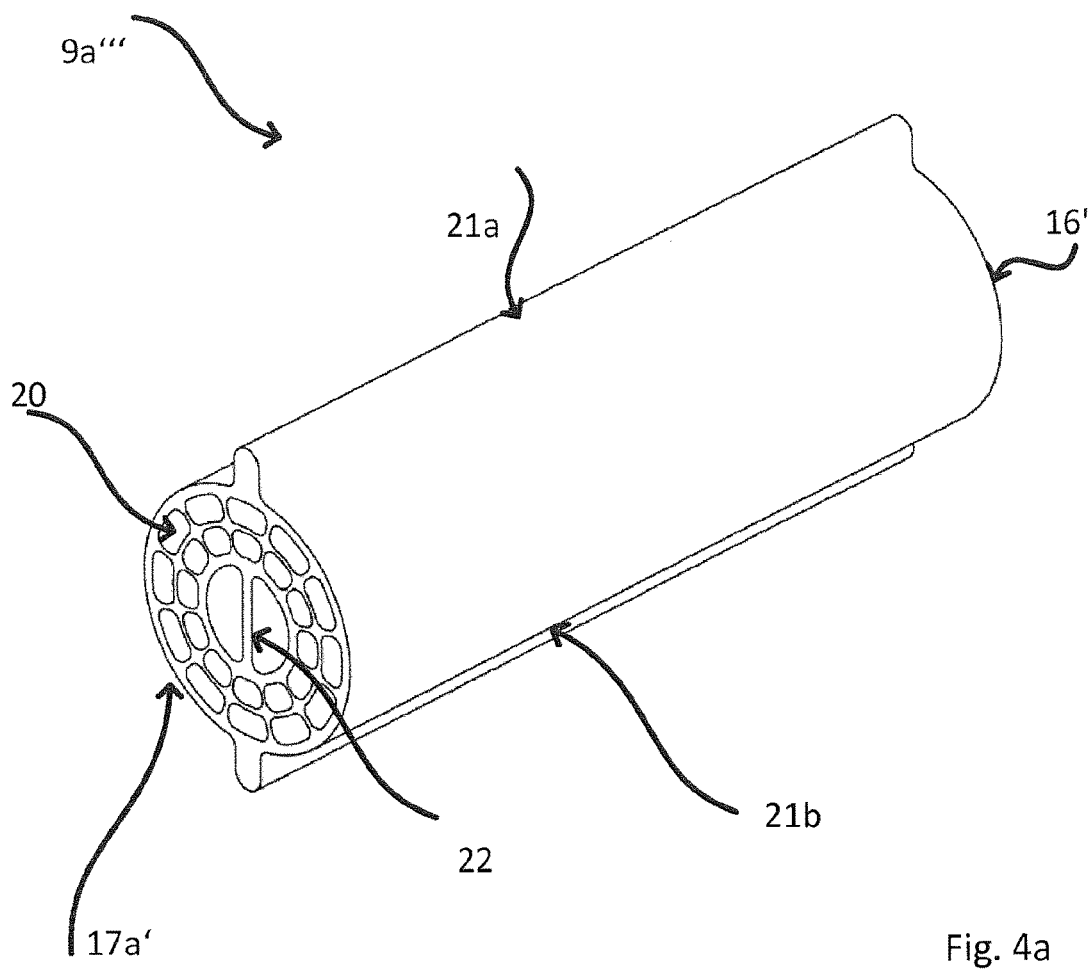
FIG. 4 is a second embodiment of a measuring tube of the invention with vibration damping hollow ducts, a flow forming module and two stiffness influencing fins, in (a) perspective view and (b) in a sectional illustration.
Figure 4B:
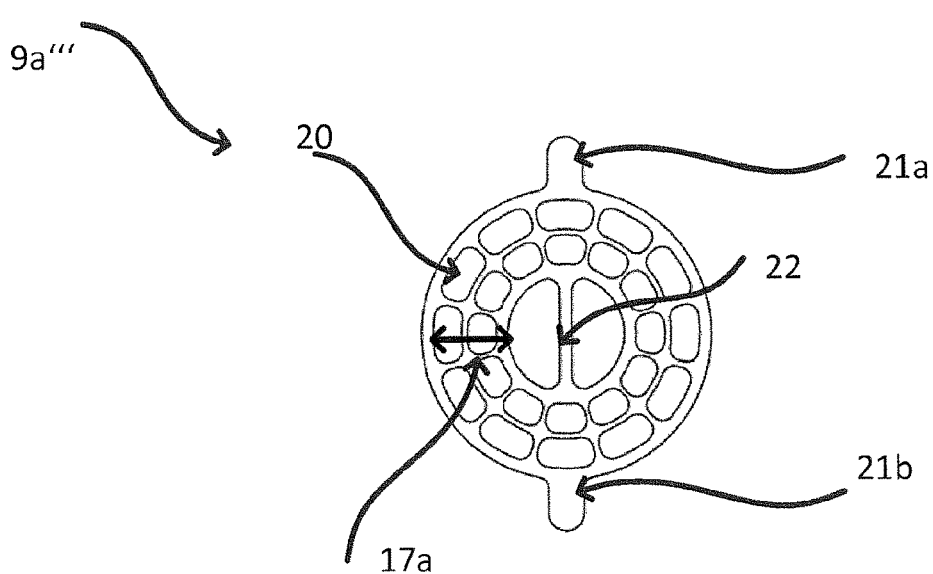

A third example of an embodiment for a measuring tube 9a''' is the subject matter of FIG. 4, wherein FIG. 4a is a perspective view and FIG. 4b is a sectional illustration. Arranged externally on the measuring tube 9a''' are two fins 21a, 21b, which extend externally from its wall 16' on oppositely lying sides and provide a direction dependent stiffness of the measuring tube 9a'''. Further visible within the wall of the measuring tube 9a''' with the wall thickness 17a' are structures 20. These structures can be, for example, either hollow ducts extending essentially parallel to the internal volume of the measuring tube 9a''' or individual, closed capsules, in given cases, filled with a powder.

Arranged in the inner space of the measuring tube 9a''' is a flow forming module, or structure 22. In the case of a flow forming module, it can be, for example, a partition or a flow rectifier. Also a number of such modules can be integrated in the same measuring tube $9a'''$, especially the internal volume of the measuring tube $9a'''$ can be subdivided into as many fine, individual tubes as desired, similarly as in the case of multi-wire electrical cables.

The wall $17a'$ of the measuring tube $9a'''$, the two fins $21a,21b$, and the flow forming module 22 are manufactured together as one piece. In the same manufacturing step, furthermore, likewise the structures 20 were formed in the wall $17a'$ of the measuring tube $9a'''$.

Figure 5:
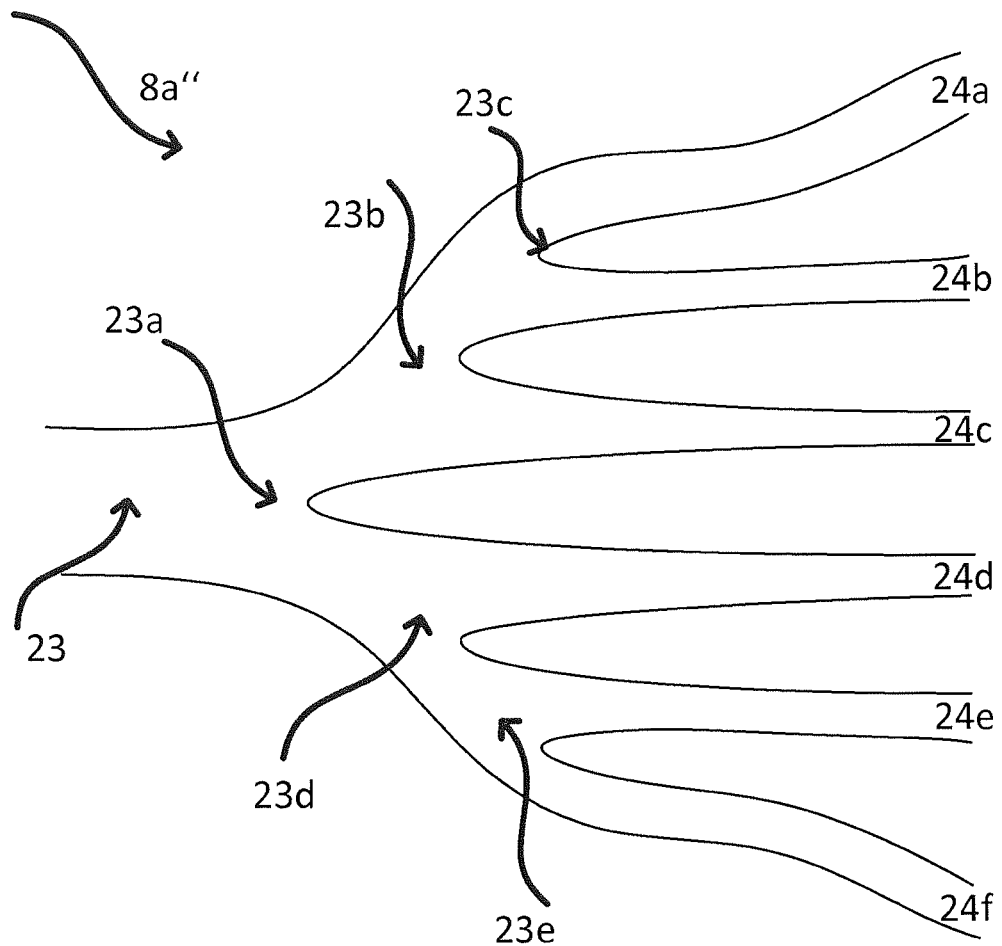
FIG. 5 is a distributor piece of the invention with a number of branches.

FIG. 5 shows a possible embodiment for a distributor piece $8a''$ of the invention, which distributes the flow volume of the medium from the pipeline, which opens into the inlet 23 of the distributor piece $8a''$, to 6 individual tubes $24a$-$f$. The distributor piece $8a''$ includes a multiply branched, continuous internal volume 23. The individual branches $23a$-$e$ divide the respective preceding section, in each case, into two subsections. The example shown here has five asymmetric branches $23a$-$e$. Of course, also distributor pieces $8a''$ with symmetric or partially symmetric branches, or with branches with one to three or more sections, and still many other examples are possible.

Figure 6:
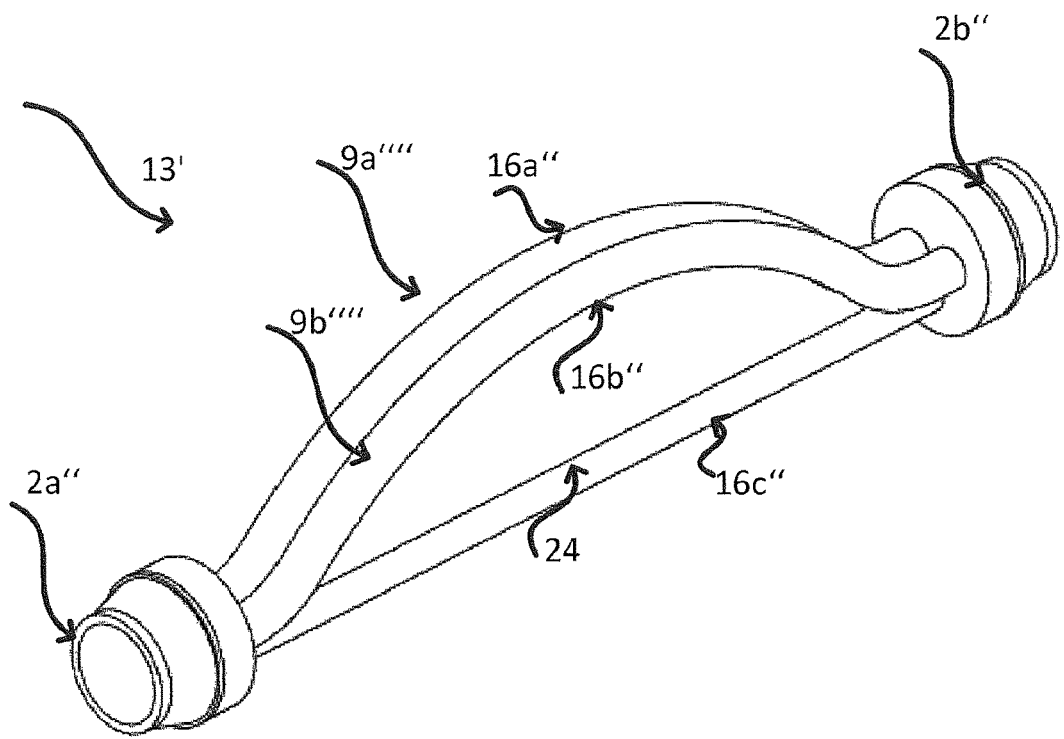
FIG. 6 is a curved measuring tube of the invention with a bypass line.

A fourth example of an embodiment for a measuring transducer $13'$ with two curved measuring tubes $9a'''',9b''''$ is shown in FIG. 6. The walls $16a'', 16b''$ of the two measuring tubes $9a'''', 9b''''$, the two process connections $2a''$ and $2b''$, the two distributor pieces (not visible in this Fig.) as well as the wall $16c''$ of a straight bypass line 24 are manufactured together as one piece. A determinable portion of the flowing medium can be diverted through bypass line 24. Then a further sensor element 32 (compare FIG. 9) can be integrated within the bypass line 24, for example, for registering an additional process variable.

Figure 7:
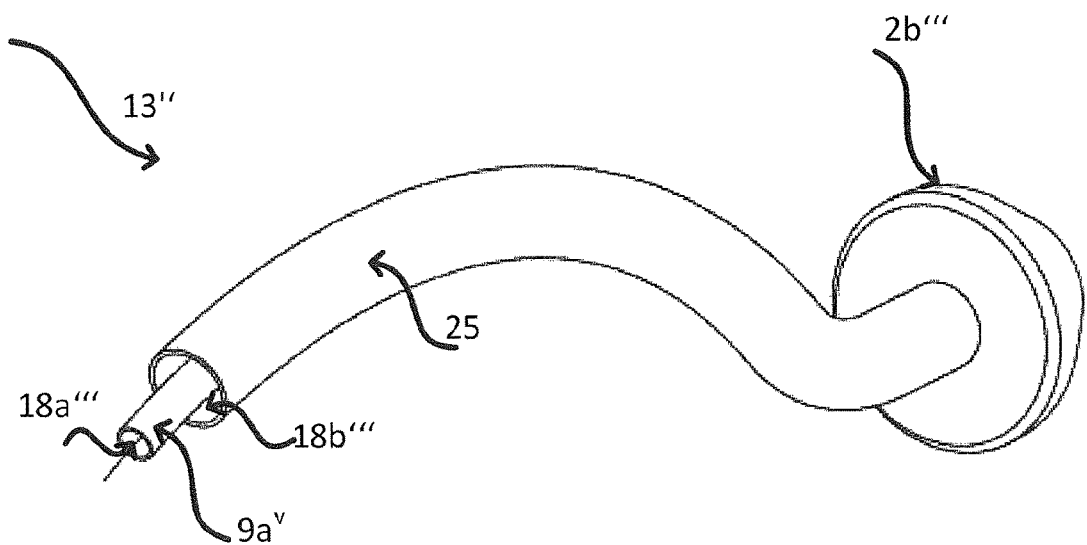
FIG. 7 is a measuring transducer manufactured of one piece with vibration absorbing tube.

In the case, in which the particular field device has only one measuring tube $9a^V$, a vibration absorbing tube 25 is provided supplementally to the single measuring tube $9a^V$, such as shown, for example, in FIG. 7. In the example shown here, the vibration absorbing tube 25 has a greater diameter, thus a greater surface area of the cross sectional area $18b''$, than the measuring tube $9a^V$. The measuring tube $9a^V$ is integrated contactlessly in the interior of the vibration absorbing tube 25, and is coaxially surrounded by the vibration absorbing tube. The measuring tube $9a^V$, the vibration absorbing tube 25, as well as the two process connections $2a''',2b'''$ (only one shown) are manufactured together and as one-piece by means of the generative method.

Figure 8:
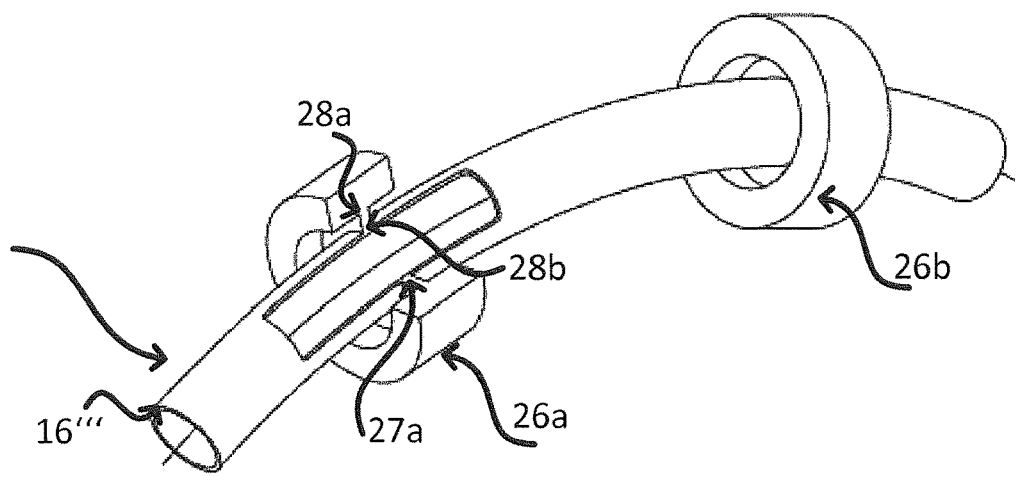
FIG. 8 is a measuring tube of the invention with mass elements.

Another opportunity for targeted influencing of the properties of a measuring tube $9a^{VI}$ is shown in FIG. 8. Advantageously, the mass, respectively the mass distribution, of the measuring tube $9a^{VI}$ can be changed in the shown manner, without thereby influencing the stiffness of the measuring tube. In this way, the position of the respective oscillation modes within the frequency spectrum of the measuring tube $9a^{VI}$ can be varied.

Arranged on the external region of the wall $16'''$ of the measuring tube $9a^{VI}$ are, by way of example, two mass elements $26a,26b$. The first mass element $26a$ is sectioned in the selected representation, in order to make the securement unit $27a,27b$ applied in each case visible, by means of which securement unit $27a,27b$ the mass element $26a$ is secured externally on the wall $16'''$ of the measuring tube $9a^{VI}$. In the example shown here, the securement unit $27a,27b$ is a ring radially surrounding the measuring tube $9a^{VI}$. However, also struts extending parallel or perpendicular to the flow direction of the medium or fins extending along the wall of the at least one measuring tube $9a^{VI}$ parallel to the flow direction or still other geometries can be used. In order that the stiffness of the measuring tube $9a^{VI}$ remains essentially constant, the contact area $28a$ between the securement unit $27a$ and the mass element $26a$ and/or the contact area $28b$ between the securement unit $27a$ and the external region of the wall $16'''$ of the measuring tube $9a^{VI}$ should be kept minimal. Both the measuring tube $9a^{VI}$, as well as also the mass elements $26a,26b$ and the securement units $27a,27b$ are manufactured together as one-piece by means of the generative method.

Figure 9:
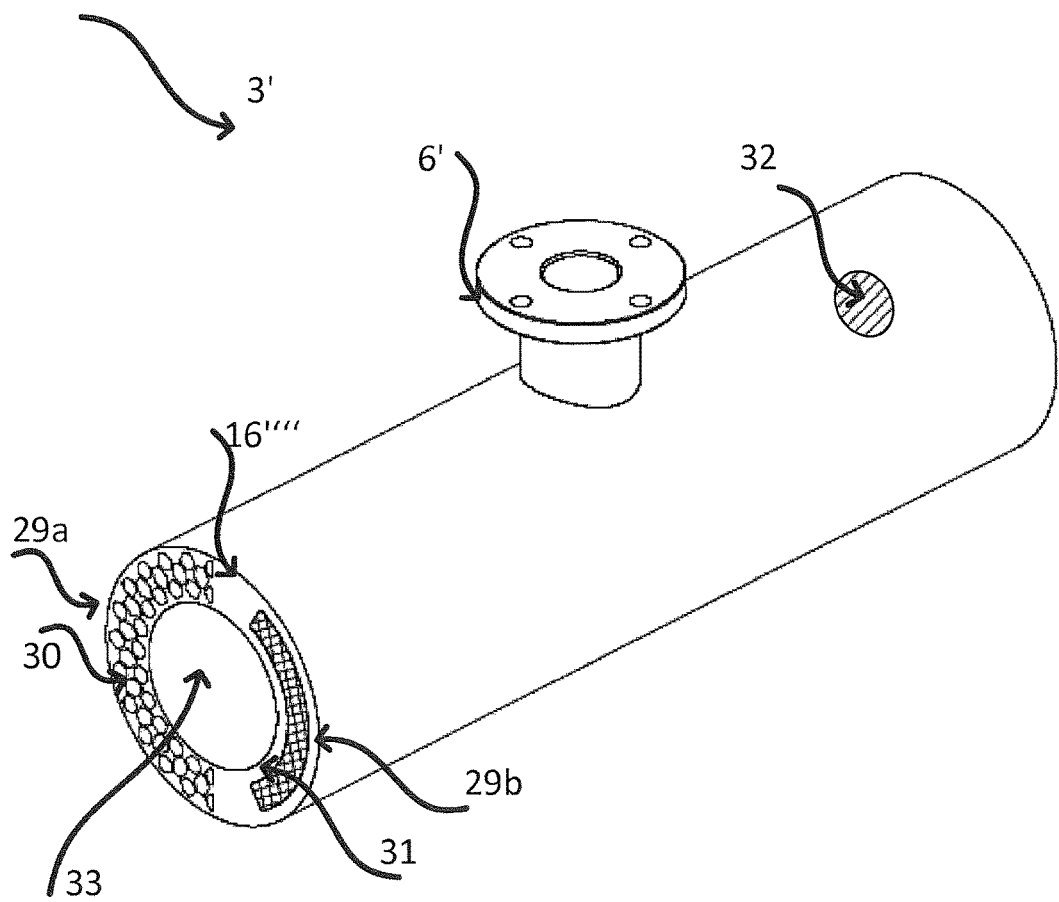
FIG. 9 is an anisotropic housing of the invention with a feedthrough for the electronics unit and an additional sensor.

Also different advantageous options are available for the transducer housing $3'$, such as shown in FIG. 9, by way of example. Provided within the wall $16''''$ of the transducer housing $3'$ are, as in the case of the measuring tube $9a'''$ of FIG. 4, structures $20'$. They can be, for example, hollow ducts or empty/filled capsules. The wall $16''''$ of the transducer housing $3a'$ of FIG. 9 has, for example, an anisotropic structure. In a first portion $29a$ within the wall $16''''$ a beehive structure 30 is present, while in a second portion $29b$ a composite material 31 is provided. Using such a construction, an anisotropic stiffness—and, in given cases, also an anisotropic mass distribution can be achieved, in such a manner that regions, which are exposed to an increased external force have, for example, a greater stiffness. Such regions are, for example, especially regions, in which the process connections ($2a,2b$) and/or distributor pieces ($8a,8b$) (not shown) are integrated. Besides different portions $29a,29b$ with different structures $20'$, it is likewise an option for an anisotropic embodiment of a transducer housing $3'$ to vary the density of the used materials, or the wall thickness $17a''''$ (not shown) of the transducer housing $3'$ in certain regions.

The housing includes supplementally a neck tube $6'$, by means of which an electronics unit $6a$ (not shown) can be mounted on the transducer housing $3'$. This neck tube $6'$ is an optional component of the transducer housing $3'$. Optionally integrated, furthermore, into the wall $16''''$ of the transducer housing $3'$ can be a supplemental sensor element 32, which can be utilized for registering an additional process variable, especially temperature or pressure. A corresponding sensor element 32 can, however, also be integrated in other components of a measuring transducer 15, for example, in a bypass line 24, such as shown in FIG. 6. Hollow spaces within the transducer housing $3'$ can, finally, optionally be provided with a filling 33, especially a filling with damping properties. The filling can have, for example, a beehive structure or a porous structure. The wall $16''''$ of the transducer housing $3'$, the neck tube $6'$ and the additional sensor element 32 are manufactured together as one piece by means of the generative method.

The invention claimed is:

1. A method for manufacturing at least one component of a measuring transducer of a vibration-type for registering or monitoring at least one process variable of a flowing medium guided in a pipeline, the measuring transducer at least includes:
   a housing module, which is designed to be coupled mechanically with the pipeline via an inlet end and an outlet end, and a sensor module having at least one measuring tube held oscillatably in said housing module and caused to oscillate, at least at times, the method comprises:
   manufacturing the at least one component by means of a primary forming process, based on a digital data set, which gives at least one of shape, material or structure of the at least one component.

2. The method as claimed in claim 1, wherein:
for determining said at least one of shape, structure or material of the at least one component, the geometry, mass distribution, or stiffness of the at least one component are/is set in such a manner that a predeterminable condition is fulfilled.

3. The method as claimed in claim 1, wherein:
stiffness of the at least one component is kept constant, while at least one frequency corresponding to one of the oscillation modes of the at least one component is set to a predeterminable value.

4. The method as claimed in claim 1, wherein:
at least one frequency corresponding to one of the oscillation modes of the at least one component is kept constant, while at least the stiffness is set to a predeterminable value.

5. The method as claimed in claim 1, wherein:
at least one of mass distribution, stiffness or geometry of the at least one component is selected in such a manner that at least one frequency corresponding to one of the oscillation modes of the housing module and at least one frequency corresponding to one of the oscillation modes of the sensor module are different from one another.

6. The method as claimed in claim 1, wherein:
the at least one component is the at least one measuring tube flowed through by the fluid; and
at least one of mass distribution, stiffness or geometry of the at least one measuring tube is selected in such a manner that the flow profile is conditioned and at least one disturbance effect evoked by the flow of the medium is minimized.

7. The method as claimed in claim 1, wherein:
the primary forming process for manufacturing the at least one component is selective laser sintering, selective laser melting, laser deposition welding, a metal powder application method, fused deposition modeling, multi jet modeling, colorjet printing, or LaserCUSING.

8. The method as claimed in claim 1, wherein:
the digital data set, which gives said at least one of shape, structure or material of the at least one component, is transmitted to a customer; and
the at least one component is manufactured on-site at the customer's location by means of a primary forming process.

9. The method as claimed in claim 1, wherein:
the least one component is manufactured by means of a layered applying of a powder.

10. The use of a measuring transducer of the vibration-type as claimed in claim 1, wherein:
in a measuring device for registering or monitoring at least one process variable of a flowable medium guided in a pipeline.

11. The method as claimed in claim 2, wherein:
for determining said at least one of shape, structure, material of the at least one component, the geometry, mass distribution or stiffness of the at least one component are/is set by means of an iterative simulation.

12. The method as claimed in claim 11, wherein:
for determining said at least one of shape, structure, material of the at least one component, the geometry, mass distribution or stiffness of the at least one component are/is set by means of a finite elements simulation.

13. The method as claimed in claim 1, wherein:
the least one component is manufactured by means of a layered melting-on of a powder.

14. The method as claimed in claim 9, wherein:
the powder is a metal powder.

15. The method as claimed in claim 13, wherein:
the powder is a metal powder.

* * * * *